United States Patent [19]

Savage

[11] Patent Number: 4,965,818

[45] Date of Patent: Oct. 23, 1990

[54] RADIOSCOPIC LAVATORY CHAIR AND METHOD

[76] Inventor: Timothy L. Savage, 4536 Garwood St., Ladson, S.C. 29456

[21] Appl. No.: 420,770

[22] Filed: Oct. 10, 1989

[51] Int. Cl.⁵ .............................................. H05G 1/00
[52] U.S. Cl. .................................... 378/208; 378/156
[58] Field of Search ........................ 378/178, 208, 156

[56] References Cited

FOREIGN PATENT DOCUMENTS 2351543 4/1975 Fed. Rep. of Germany ...... 378/178

Primary Examiner—Craig E. Church
Attorney, Agent, or Firm—Senniger, Powers, Leavitt and Roedel

[57] ABSTRACT

A lavatory chair adapted to support a patient during radioscopic imaging of defecation dysfunction of the patient. The chair comprises an open-bottomed seat portion, a support structure for supporting the seat portion, a screen having a preselected radiopacity, and a mechanism for mounting the screen to the seat portion to give the seat portion approximately the same radiopacity as an average patient. The method of using the lavatory chair is also disclosed.

18 Claims, 4 Drawing Sheets

RADIOSCOPIC LAVATORY CHAIR AND METHOD

BACKGROUND OF THE INVENTION

This invention relates generally to lavatory chairs, and in particular to lavatory chairs for use during radiographic imaging.

Radiographic analysis is used to diagnose defecation dysfunction of patients. During such analysis it is important that a patient be in a sitting or squatting position. Thus, a chair is generally provided. However, if the chair has a radiopacity much greater than that of the patient, the radiographic image tends to be underexposed. If the chair has a radiopacity much less than that of the patient the radioscopic image tends to be overexposed.

Two types of chairs have been used each having a radiopacity corresponding to that of an average patient. One of these chairs has a seat portion constructed of solid wood. The other has a seat portion that is hollow, but filled with a liquid such as water.

A disadvantage of such chairs is that they are heavy and, therefore difficult to move. Another disadvantage is that although the radiopacities of patients may be quite diverse, i.e., a large patient will have a relatively high radiopacity and a small patient will have a relatively small radiopacity, the radiopacity constant of each chair cannot be altered. Thus, the radiographic image formed during use of these prior art chairs may be over-illuminated or under-illuminated and, therefore, lack sufficient contrast for proper analysis.

SUMMARY OF THE INVENTION

Among the objects of the present invention may be noted the provision of an improved lavatory chair for supporting a patient during radiographic analysis of defecation dysfunction; the provision of such a chair which is lightweight; the provision of such a chair which has an adjustable radiopacity; and the provision of such a chair which is of relatively simple and inexpensive construction.

Generally, a lavatory chair of the present invention is adapted to support a patient during radioscopic analysis of defecation dysfunction of the patient. The chair comprises an open-bottomed seat portion, a support structure for supporting the seat portion, a screen having a preselected radiopacity, and means for mounting the screen to the seat portion and between the seat portion and a radiographic device. The screen gives the seat portion approximately the same radiopacity as an average patient.

In a second aspect of this invention, the lavatory chair comprises an open bottomed seat portion, a support structure for supporting the seat portion, and means for varying the radiopacity of the seat portion according to the radiopacity of the patient.

In a third aspect of this invention, the lavatory chair comprises a seat having an opening therein, a support for the seat, a set of screens of preselected radiopacities, and means for mounting one or more of the screens between the seat and the radiographic device to adjust the radiopacity of the seat according to the radiopacity of the patient.

With the lavatory chair of the present invention, as long as the screen has a sufficient radiopacity the chair itself can be constructed of lightweight material. Thus, the chair is easily moved and handled. Also, the radiopacity of the chair can be varied to match the radiopacity of the patient, thus, the resulting images are improved, facilitating analysis.

These and other advantages will be in part apparent and in part pointed out hereinafter.

BRIEF DESCRIPTION OF THE DRAWINGS

Corresponding reference numerals indicate corresponding parts throughout the several views of the drawings.

DETAILED DESCRIPTION OF THE PREFERRED EMBODIMENT

Figure 1:
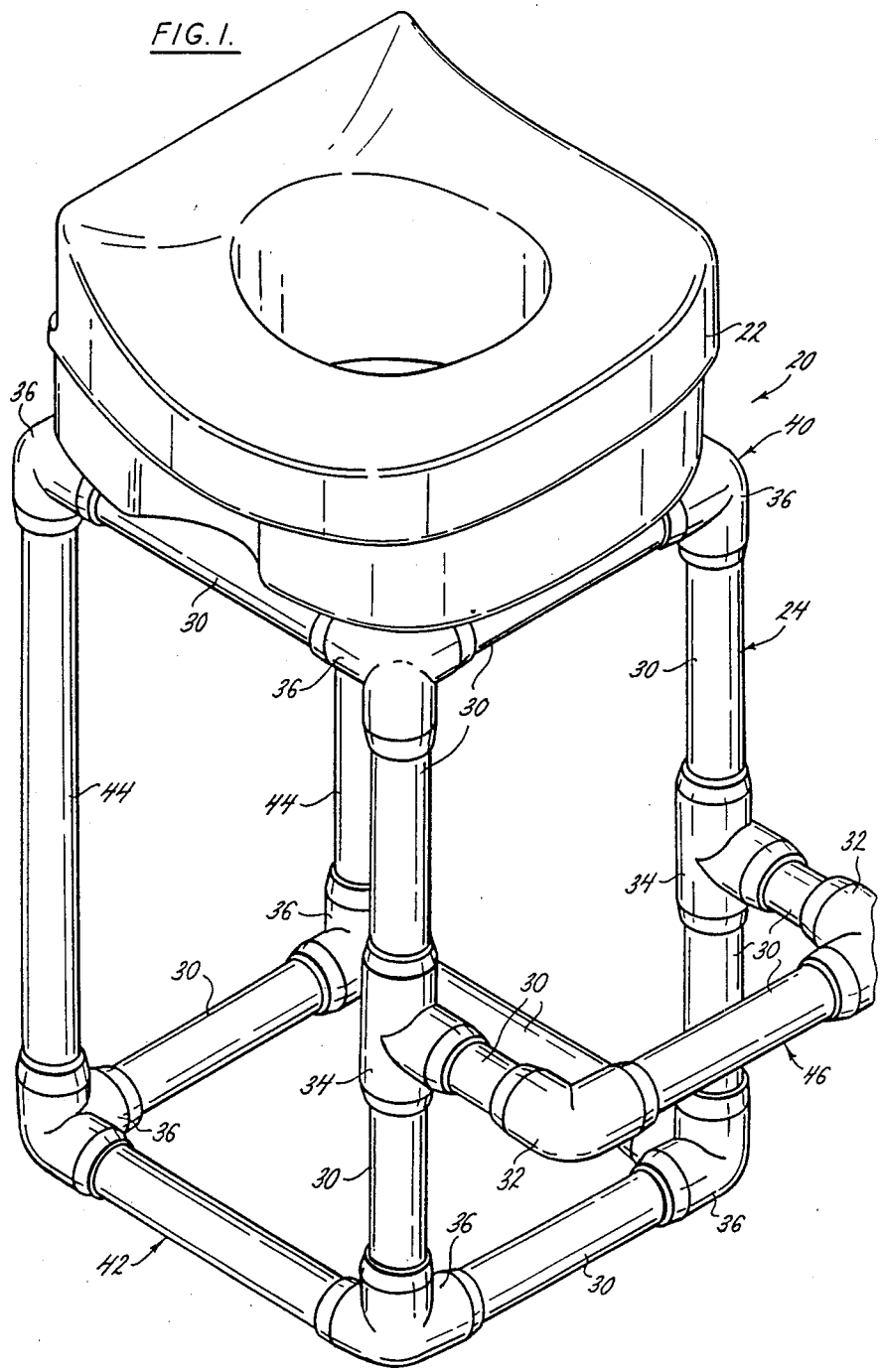
FIG. 1 is a perspective view of a lavatory chair of the present invention.

A lavatory chair constructed according to the principles of this invention is indicated generally at 20 in FIGS. 1-4. The chair 20 is adapted for supporting a patient during radioscopic analysis of defecation dysfunction of the patient. It comprises an open-bottomed seat portion 22, a support structure 24 for supporting the seat portion 22, and plates 26 of preselected radiopacity secured to the seat portion 22.

The support structure 24 is formed from a plurality of tubular members 30, elbow connectors 32, T-connectors 34, and corner connectors 36. Preferably, the tubular members and connectors are made of a sturdy lightweight material such as PVC. The support structure 24 has a top portion designated generally at 40, a base portion designated generally at 42, vertical risers 44 connecting the top portion 40 to the base portion 42, and a foot rest designated generally at 46. During radioscopic imaging, the support structure 24 is out of the field of view of the radioscopic device, thus, the radiopacity of the support structure 24 is unimportant.

Figure 2:
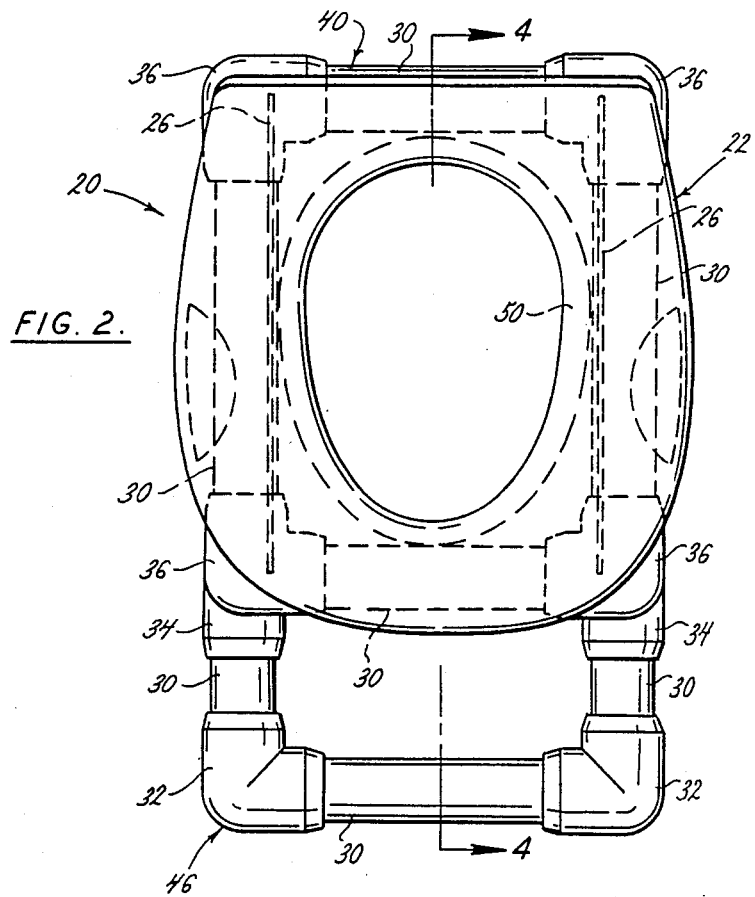
FIG. 2 is a top plan view of the lavatory chair.
Figure 5:
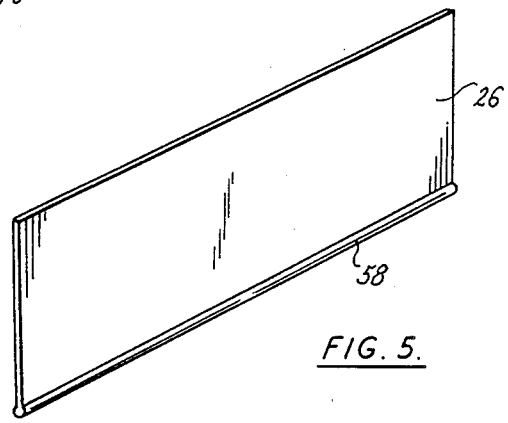
FIG. 5 is a perspective view of a rigid plate adapted to be inserted into the seat portion of the chair.
Figure 3:
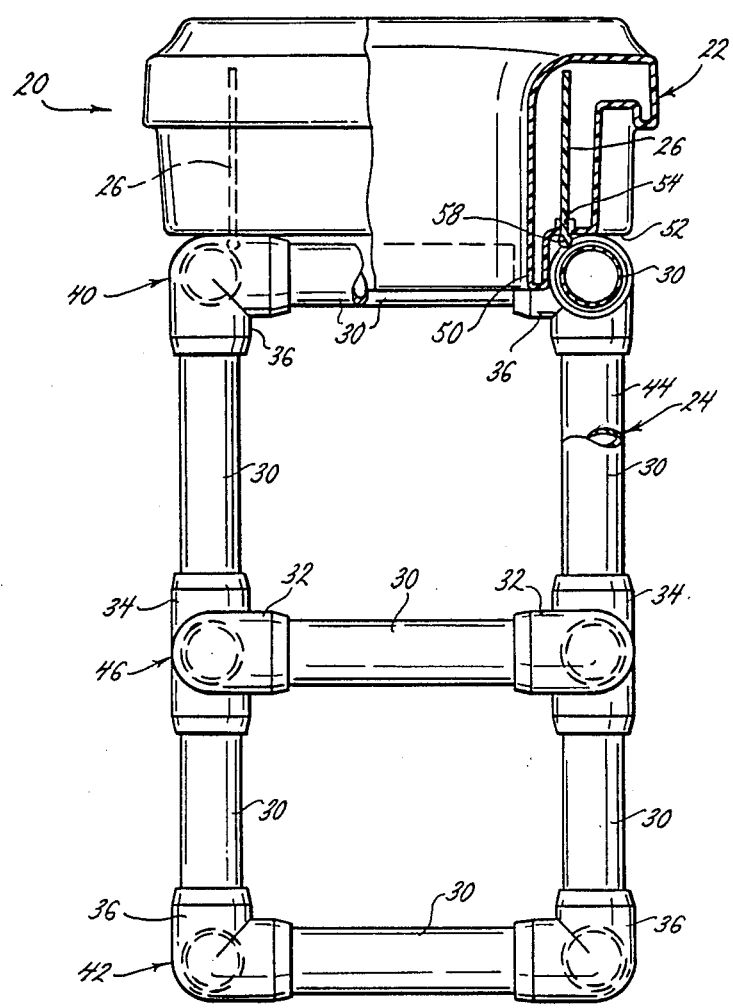
FIG. 3 is a front elevational view, in partial section, showing a screen within the seat portion of the lavatory chair.
Figure 4:
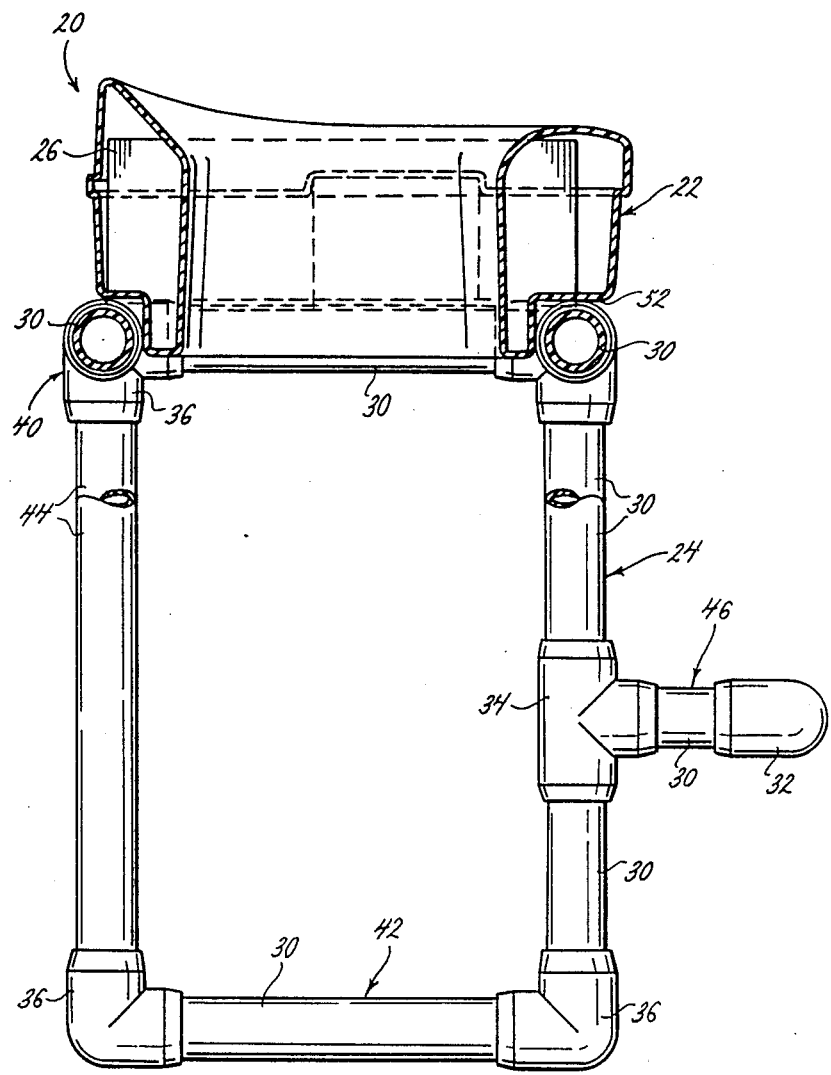
FIG. 4 is a cross-sectional view taken along line 4—4 of FIG. 2.

The seat portion 22 is preferably formed of a plastic material. It includes a lower surface 52, a lip or rim 50 extending downwardly from the lower surface 52, and slots 54 (shown in FIG. 3) through the lower surface 52 for receiving the rigid plates 26. The lower surface 52 of the seat portion 22 abuts the top portion 40 of the support structure 24. As shown in FIG. 2, the rim 50 fits snugly within the perimeter of the top portion 40 of the support structure 24. Preferably, the seat portion 22 is secured to the support structure 24 by the friction between the rim 50 and the top portion 40 of the support structure 24. Such securement enables the seat portion 22 to be quickly removed from the support structure 24 for accessing the slots 54.

The plates 26 extend upwardly through the slots 54 and are frictionally held in place. Preferably, the plates 26 have beads 58 on their lower edges to enable the plates 26 to be grasped by a user and, thereby, slid in or out of the slots 54. The plates 26 act as radiation filters or screens attenuating radiation and, thereby, increasing the radiopacity of the seat portion 22 during radioscopic imaging. The slots 54 constitute means for releasably mounting screens on the seat portion 22.

The radiopacity of the plates 26 depends upon, among other things, their thickness and material of construction. A thicker plate has a greater radiopacity that does a thinner plate. Thus, the radiopacity of the seat portion 22 can be varied by replacing at least one of the plates 26 with a plate having a different thickness. Since the seat portion 22 is made of plastic it is somewhat elastic and, as a result, the slots 54 can accommodate plates of varying thicknesses. Thus, the slots 54 and plates 26 constitute means for varying the radiopacity of the seat portion 22.

To maximize the effectiveness of the radiographic analysis, it is important that the seat portion 22 have approximately the same radiopacity as that of the patient. The radiopacity of the patient depends upon the size of the patient. The larger the patient the greater is his or her radiopacity. It is believed a ⅜" thick steel plate has approximately the same radiopacity as an average size patient. The seat is preferably constructed so that its radiopacity (without a plate) is very low. Thus, a seat portion 22 in which a ⅜" thick steel plate is inserted through one of the slots 54 has approximately the same radiopacity as that of an average size patient. If the patient is large, the ⅜" thick plate could be replaced with a thicker plate or one or more additional plates could be inserted into the other slot 54. Likewise, if the patient is small, the plate could be replaced with a thinner plate. Thus, the radiopacity of the seat portion 22 is variable according to the radiopacity of the patient.

In operation, the chair 20 is clamped to a footboard of an X-ray table. A patient sits on the seat portion 22 of the chair 20 and X-rays are taken. A plate 26 is selected according to the patients size, either by girth or weight, and is inserted in one of the slots 54 of the seat portion 22 to give the seat portion 22 approximately the same radiopacity as the patient. Thus, the seat portion 22 does unduly impair the X-ray image. To change the radiopacity, the seat portion 22 is first removed from the support structure 24. The plate 26 is removed from the slot 54 and replaced with a plate having a different radiopacity (or, alternatively, one or more plates are inserted in the other slot 54 so that the combined radiopacity of the plates matches the radiopacity of the patient). Thus, the radiopacity of the seat portion 22 is variable to accommodate patients of different sizes. Moreover, since the chair 20 is made of PVC and plastic or other lightweight materials, it is lightweight and easily transportable.

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense.

What is claimed is:

1. A lavatory chair adapted to support a patient during radiroscopic imaging of defecation dysfunction of the patient, the chair comprising an open-bottomed seat portion, a support structure for supporting the seat portion, a screen having a preselected radiopacity, means for mounting the screen to the seat portion to give the seat portion approximately the same radiopacity as an average patient.

2. The lavatory chair according to claim 1 wherein the mounting means comprises means for releasably mounting the screen on the seat portion.

3. The lavatory chair according to claim 2 wherein the means for releasably mounting the screen on the seat portion comprises means for releasably engaging one of a plurality of screens of varying radiopacities to vary the radiopacity of the seat portion according to the radiopacity of the patient.

4. The lavatory chair according to claim 2 wherein the screen comprises a generally rigid plate.

5. The lavatory chair according to claim 4 wherein the mounting means is adapted for mounting one of a plurality of plates each having a different radiopacity to vary the radiopacity of the seat portion according to the radiopacity of the patient.

6. A lavatory chair adapted to support a patient during radioscopic analysis of defecation dysfunction of the patient, the chair comprising an open bottomed seat portion, a support structure for supporting the seat portion, and means for varying the radiopacity of the seat portion to accommodate patients of different radiopacities.

7. The lavatory chair according to claim 6 wherein the means for varying the radiopacity of the seat comprises means for releasably mounting a screen of preselected radiopacity between the seat portion and a radioscopic device.

8. The lavatory chair according to claim 7 wherein the mounting means is adapted for engaging at least one of a plurality of screens each having a different radiopacity to vary the radiopacity of the seat portion according to the radiopacity of the patient.

9. The lavatory chair according to claim 8 wherein the mounting means comprises a slot in the seat portion dimensioned for receiving at least one of the screens.

10. The lavatory chair according to claim 9 wherein the screen comprises a generally rigid plate.

11. The lavatory chair according to claim 6 wherein the varying means comprises means for releasably securing at least two screens to the seat portion to change the radiopacity of the seat portion.

12. The lavatory chair according to claim 11 wherein the screens comprise generally rigid plates.

13. A lavatory chair adapted to support a patient during radioscopic analysis of defecation dysfunction of the patient, the chair comprising a seat having an opening therein, a support for the seat, a set of screens of preselected radiopacities, and means for mounting one or more of the screens between the seat and the radioscopic device to adjust the radiopacity of the seat according to the radiopacity of the patient.

14. The lavatory chair according to claim 13 wherein the mounting means comprises a slot in the seat portion adapted for receiving the screen.

15. The lavatory chair according to claim 14 wherein the screen comprises a generally rigid plate.

16. An improved method of radioscopic imaging of defecation dysfunction of a patient comprising the steps of:
   providing a seat to support the patient during the imaging;
   adjusting the radiopacity of the seat to approximate the radiopacity of the patient;
   making radioscopic images of the patient while the patient is supported on the seat.

17. The method according to claim 16 wherein the step of adjusting the radiopacity of the seat comprises the steps of:
- selecting a filter from a plurality of filters each having a different radiopacity; and
- securing the filter to the seat portion to give the seat portion a total radiopacity approximating that of the patient.

18. The method according to claim 16 wherein the step of adjusting the radiopacity of the seat comprises the steps of:
- selecting one or more filters from a plurality of filters each having a different radiopacity; and
- securing the filters to the seat portion to give the seat portion a total radiopacity approximating that of the patient.

* * * * *